United States Patent [19]

Hopkins et al.

[11] Patent Number: 5,653,695
[45] Date of Patent: Aug. 5, 1997

[54] WATER SOLUBLE LUBRICANT FOR MEDICAL DEVICES

[75] Inventors: David P. Hopkins, Salt Lake City; Mohammad A. Khan, Sandy, both of Utah

[73] Assignee: Becton Dickinson and Company, Franklin Lakes, N.J.

[21] Appl. No.: 670,296

[22] Filed: Jun. 27, 1996

Related U.S. Application Data

[63] Continuation of Ser. No. 294,212, Aug. 22, 1994, abandoned.

[51] Int. Cl.⁶ .................................................. A61M 25/00
[52] U.S. Cl. ......................... 604/265; 514/63; 428/447
[58] Field of Search ........................ 604/113, 265, 604/266; 424/401; 514/63; 428/447, 451, 425.5

[56] References Cited

U.S. PATENT DOCUMENTS

| | | |
|---|---|---|
| 3,574,673 | 4/1971 | Schweiger et al. . |
| 3,912,665 | 10/1975 | Spitzer ................................ 260/2.5 E |
| 4,588,398 | 5/1986 | Daugherty et al. . |
| 4,661,300 | 4/1987 | Daugherty . |
| 4,664,657 | 5/1987 | Williamitis et al. . |
| 4,758,595 | 7/1988 | Ogunbiyi et al. . |
| 4,814,231 | 3/1989 | Onohara ............................. 428/425.5 |
| 4,836,986 | 6/1989 | Ogunbiyi et al. . |
| 4,837,047 | 6/1989 | Sato ..................................... 422/41 |
| 4,838,876 | 6/1989 | Wang .................................. 604/265 |
| 4,842,889 | 6/1989 | Hu et al. ............................. 427/38 |
| 4,844,986 | 7/1989 | Karakelle et al. .................. 428/447 |
| 4,904,433 | 2/1990 | Williamitis . |
| 4,973,643 | 11/1990 | O'Lenick, Jr. ..................... 528/15 |
| 5,013,717 | 5/1991 | Solomon et al. ................... 514/56 |
| 5,026,607 | 6/1991 | Kiezulas ............................. 428/423 |
| 5,037,419 | 8/1991 | Valentine ............................ 604/408 |
| 5,043,161 | 8/1991 | Scarpelli ............................. 424/401 |
| 5,047,159 | 9/1991 | Zehler ................................ 252/49 |
| 5,061,738 | 10/1991 | Solomon et al. ................... 523/100 |
| 5,071,706 | 12/1991 | Soper ................................. 428/402.2 |
| 5,185,006 | 2/1993 | Williamitis et al. . |
| 5,266,359 | 11/1993 | Spielvogel ......................... 604/265 |
| 5,272,012 | 12/1993 | Opolski .............................. 604/265 |
| 5,336,209 | 8/1994 | Porzilli .............................. 604/307 |
| 5,338,312 | 8/1994 | Montgomery ..................... 604/230 |
| 5,344,411 | 9/1994 | Domb et al. ....................... 604/265 |
| 5,383,903 | 1/1995 | Totakura ............................ 604/265 |
| 5,409,463 | 4/1995 | Thomas et al. .................... 604/167 |

OTHER PUBLICATIONS

Union Carbide Chemicals and Plastic Company, Inc., Material Safety Data Sheet for Y-12686, Effective Date Jun. 1, 1992, Danbury, CT.

Union Carbide Chemicals and Plastic Company, Inc., Material Safety Data Sheet for Y-12613, Effective Date Sep. 17, 1992, Danbury, CT.

Hoffman-LaRoche, Inc., Material Safety Data Sheet for d,1-alpha-Tocopheral, Effective Jul. 20, 1992, Nutley, NJ.

W. Nikolowski, Vitamin E. in Dermatology, Vitamins, pp. 1-6, 1973.

ICI Americas Inc., Cosmocil CQ Brochure.

ICI Americas Inc., Baquacil Brochure.

Union Carbide Chemicals and Plastics Company Inc., Silwet Surfactants Brochure.

The United States Pharmacopeia, pp. 1451-1453, 1990, Rockville, MD.

*Primary Examiner*—Michael Powell Buiz
*Assistant Examiner*—Chalin Smith
*Attorney, Agent, or Firm*—Eric M. Lee, Esq.

[57] ABSTRACT

This invention relates to a new water soluble lubricant for a medical device, such as a catheter and an introducer needle. The lubricant is a silicone surfactant, which is non-ionic and which is a good lubricating fluid. Preferably the silicone surfactant that is used is a block copolymer polyalkylene oxide-modified polydimethylsiloxane. The lubrication solution includes a solution stabilizer to clarify the solution and antimicrobial agents to inhibit microbial growth in the water solution or on the coated product. Vitamin E or its derivatives may also be used in the lubrication solution.

3 Claims, No Drawings

WATER SOLUBLE LUBRICANT FOR MEDICAL DEVICES

This application is a continuation of application Ser. No. 08/294,212, filed Aug. 22, 1994, now abandoned.

BACKGROUND OF THE INVENTION

This invention relates in general to a novel lubricant for intravenous (IV) catheters. IV catheters are generally used on patients to infuse liquids, such as normal saline, glucose solutions and drugs, into the patient. These catheters are also used to withdraw blood from the patient for blood gas and other analysis.

In order to place a catheter in a patient's vein, a sharp introducer needle must be used to puncture the skin, tissue and vein wall to provide a path for placement of the catheter in the vein. Typical IV catheters are "over-the-needle" catheters where the catheter is coaxially placed over the needle. The distal tip of the catheter is located adjacent to and proximal of the sharp distal tip of the needle. Preferably the tip of the catheter adheres slightly to the tip of the needle to ensure that both the catheter and needle travel together through the skin, tissue and vein wall and into the patient's vein. The adherence is achieved by making the inner diameter of the catheter tip slightly smaller than the outer diameter of the needle.

Placement of the catheter and introducer needle into the patient causes sharp pain to the patient. In order to facilitate insertion of the catheter and introducer needle into the vein and to minimize patient discomfort, the catheter and needle can both be lubricated. Most IV catheters are lubricated with polydimethylsiloxane silicone fluid. However, some IV catheters are not lubricated at all.

The polydimethylsiloxane silicone fluid may be applied to the surface of the catheter and needle by wiping the surfaces with the lubricant. Alternatively, the catheter and needle can be separately dipped into a solution of polydimethylsiloxane silicone fluid and a solvent. This is generally the preferred method of applying the lubricant because a consistent, controlled and uniform coating can be achieved. The polydimethylsiloxane silicone fluid must be dissolved in an organic solvent because the silicone oil in this compound is hydrophobic. Typically, the solution contains 2.5% silicone oil. The catheter and needle are then separately dipped into this solution.

Until recently the preferred solvent has been freon because it is non-flammable and flashes off, i.e. evaporates, readily after the polydimethylsiloxane silicone fluid solution has been applied to the catheter and needle. Although freon has been preferred, it does suffer some drawbacks. For instance, the high evaporation rate of freon causes the polydimethylsiloxane silicone fluid to concentrate on the surface of the solution in which the catheter and needle are dipped. Because of this high evaporation rate, the solution is difficult to control. Moreover this solution is expensive because of the large loss of freon during the coating process. In addition, freon is a chlorofluorocarbon (CFC) which is thought to react with and destroy the earth's protective ozone layer. Thus the manufacture and use of such CFC's will eventually cease in the near future.

Other solvents will have to be used in order for silicone fluid to be applied to catheters and introducer needles as a lubricant. Other solvents include alcohol and hydrocarbons. However, alcohol and hydrocarbons are highly combustible and are therefore too dangerous for use in manufacturing.

SUMMARY OF THE INVENTION

It is therefore an object of this invention to provide a lubrication solution for a medical device, such as a catheter and an introducer needle assembly, that is inexpensive and easy to control.

It is another object of this invention to provide a lubricant for a medical device, such as a catheter and an introducer needle assembly, that does not require the use of a CFC as a solvent.

It is yet another object of this invention to provide a lubrication solution for a medical device, such as a catheter and an introducer needle assembly, that is "environmentally friendly".

It is still another object of this invention to provide a lubrication solution for a medical device, such as a catheter and an introducer needle assembly, that is not flammable.

The lubricant of this invention uses water as the solvent. The lubricant is a silicone surfactant, which is a good lubricating fluid. In addition, the silicone surfactant is preferably non-ionic because it may have lower toxicity than the ionic form. The lubrication solution may also include vitamin E or its derivatives. In addition, the lubrication solution in which the device to be lubricated is dipped includes a solution stabilizer to clarify the solution and antimicrobial agents to inhibit microbial growth in the water solution or on the coated product.

The above and other objects and advantages of the invention will be apparent upon consideration of the following detailed description.

DETAILED DESCRIPTION OF THE INVENTION

Although this invention is discussed in terms of its application to IV catheters and introducer needles, it is to be understood that this invention could be used on other medical devices where a lubricious surface on the device is desirable.

The use of a water soluble lubricant for medical devices reduces some of the problems associated with prior lubrication systems. For example, such a water based solution is relatively inexpensive and is easier to control than freon or alcohol based solutions. In addition, water soluble surfactant lubricants, like the present invention, reduce the likelihood of poor flashback through the introducer needle lumen. This is because a surfactant lubricant tends to draw blood through the needle and does not resist blood flow as most silicone fluids do. Finally, the surfactant has a higher affinity for the catheter and introducer needle. As a result, the surfactant improves coating uniformity and is less likely to be pushed out from between the catheter tip and needle, thus controlling adhesion between the catheter tip and the introducer needle tip.

This invention comprises water as the solvent. A silicone surfactant is used as the lubricant since it is a good lubricating fluid. The silicone surfactant should comprise between about 0.25% to about 40.0%, preferably from about 2.0% to about 6.0%, of the solution. The lubrication solution may also include vitamin E or its derivatives. Preferably 0.1% to about 1.0% of vitamin E or its derivative is used. The lubrication solution should also include a solution stabilizer to clarify the solution and antimicrobial agents to inhibit microbial growth in the water solution or on the coated product. The solution stabilizer should comprise between about 0.1% to about 10%, preferably about 0.2% to about 1.0%, of the solution. The antimicrobial agent should comprise between about 0.001% to about 5.0%, preferably about 0.002% to about 0.05%, of the solution.

Preferably the silicone surfactant that is used is a Silwet silicone surfactant. Silwet is the trade name of a class of silicone surfactants sold by OSI Specialties, Inc. These surfactants are polyalkylene oxide-modified polydimethylsiloxane block copolymers. They are similar to standard silicone fluids except the polydimethylsiloxane backbone has polyalkylene oxide side chains similar to non-ionic surfactants like poly-(oxyethylene) poly-(oxypropylene) block copolymers known as pluronic polyols. The side chains are terminated with either hydroxy or low alkoxy end groups. One of these surfactants, Silwet L7001 has a molecular weight of 20,000 and a viscosity of 1700 centistokes. Its chemical formula is shown below:

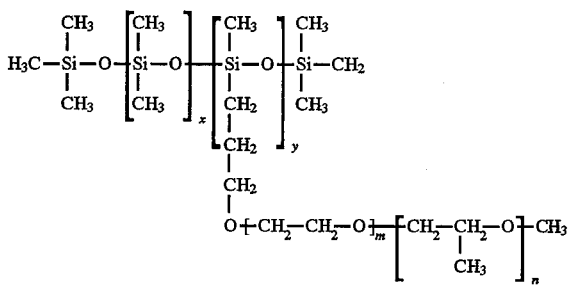

The amino-modified silicone polyether copolymer can also be used as the lubricant alone or in combination with the polyalkylene oxide-modified polydimethylsiloxane block copolymer. These surfactants are soluble in a wide variety of solvents such as CFC, alcohol, acetone, and water. The polyalkylene oxide chains also promote wetting on polyether urethane surfaces. Polyether urethane is a material that is used for making IV catheters. The similarity in chemical structure between these side chains and the soft segment of polyether urethane promote the surfactant's affinity for the catheter surface.

Although surfactants can be irritating or toxic depending on exposure levels, the Silwet silicone surfactants are copolymers of two polymeric materials, silicone fluids and polyalkylene oxides, which are low in toxicity. In particular, Silwet L7001 has a very low order of acute toxicity by swallowing, or skin penetration and is minimally irritating to the skin and is not irritating to the eyes. Thus, there should be no toxicity problems when the lubricant of this invention is used on a patient.

EXAMPLE NO. 1

Initial studies were conducted by separately dipping 20 gauge catheters and introducer needles into 4%, 8% and 32% Silwet L7001 silicone surfactant and water solutions and then assembling the catheters and needles. The assemblies were penetration tested through 13.5 mil. thick natural latex film.

|  | 4% Silwet L7001 | 8% Silwet L7001 | 32% Silwet L7001 |
| --- | --- | --- | --- |
| Needle tip (g) | 24.5 (0.9) | 23.3 (2.9) | 24.3 (5.8) |
| Needle transition (g) | 18.5 (2.7) | 17.0 (2.2) | 15.0 (1.0) |
| Needle heel (g) | 11.0 (0.7) | 10.5 (1.5) | 8.0 (0.0) |
| Catheter tip (g) | 26.0 (3.7) | 28.3 (5.3) | 25.3 (1.9) |

-continued

|  | 4% Silwet L7001 | 8% Silwet L7001 | 32% Silwet L7001 |
| --- | --- | --- | --- |
| Catheter taper (g) | 15.3 (0.8) | 15.0 (3.0) | 10.3 (0.8) |
| Catheter drag (g) | 7.3 (1.9) | 4.5 (0.5) | 4.0 (0.0) |

NOTE: ( ) = standard deviation. Sample size = 4.

The values given represent the resistance in grams when the device is penetrated through the latex membrane. These values are comparable to those of currently marketed products that are lubricated with dimethylsiloxane fluids and are better than products that are unlubricated. This example thus shows that a silicone surfactant works as a lubricant for a catheter and/or introducer needle.

Vitamin E, which is known as alpha-tocopherol, is an antioxidant and thus prevents degradation of the solution. Vitamin E and its derivative vitamin E acetate are both oily products and also enhance the lubricity of this lubrication system. The molecular structure of vitamin E is given below:

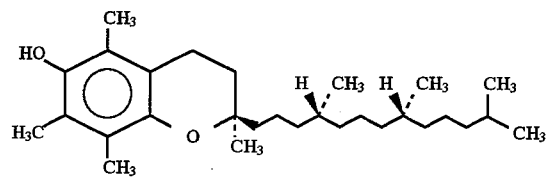

Since the lubricant solution is prepared in water, it is highly desirable that a small amount of an effective antimicrobial agent be present to serve as a preservative. In the absence of such an agent, micro-organisms may grow in the solution and make the solution toxic. There are several commercial antimicrobial agents available. These are iodophors; phenols; phenolic compounds such as para-chloro-meta-xylenol; biguanides such as chlorhexidine gluconate and polyhexamethylene biguanide hydrochloride (cosmocil). Cosmocil is used because it is less toxic than the other antimicrobial agents and is used as a preservative in contact lens cleaning solutions. The molecular structure of cosmocil is given below:

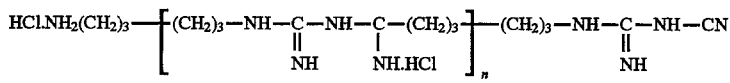

The molecular weight of this product is 2100±300.

EXAMPLE NO. 2

20 gauge catheters and needles were separately dipped in a solution containing 8% Silwet L7001 silicone surfactant, 0.25% vitamin E, 0.5% vitamin E acetate, and 0.026% cosmocil. The catheters and needles were then assembled and these assemblies were penetration tested through 13.5 mil. thick natural latex film. The results are shown below:

| Needle tip (g) | 18.3 (1.9) |
| --- | --- |
| Needle transition (g) | 14.7 (0.6) |
| Needle heel (g) | 7.0 (0.3) |
| Catheter tip (g) | 20.2 (2.3) |

-continued

| | | |
|---|---|---|
| Catheter taper (g) | 10.5 (0.6) | |
| Catheter drag (g) | 3.5 (1.3) | |

NOTE: ( ) = standard deviation. Sample size = 5

It can be seen that the use of vitamin E and/or its derivatives in the solution improve the penetration forces.

When vitamin E and/or its derivatives are included in the silicone surfactant solution, a rather cloudy solution is obtained indicating that the solution is not homogenous. If a quaternary ammonium salt is added at a certain concentration, a clear solution is obtained. For example, Sylguard, sold by Dow Corning, which is a reactive quat and benzalkonium chloride can be added to the solution. Other quaternary ammonium salts, such as benzethonium chloride, could also be used.

EXAMPLE NO. 3

A solution containing 6.0% Silwet L7001 silicone surfactant, 0.36% vitamin E and 1.0% benzalkonium chloride was used as the lubricant solution. In this example, the 1.0% benzalkonium chloride was in the form of 2.0% Hyamine 3500. Hyamine 3500 is a trade name for the benzalkonium chloride solution sold by Rohm and Hass and contains 50% of the active ingredient. As a comparison, a lubricant solution with no benzalkonium chloride was also used. 18 gauge catheters and needles were separately dipped and then assembled. These catheter assemblies were penetrated through dental dam (natural latex film).

| | No Quaternary Ammonium Salt | 1% Benzalkonium Chloride |
|---|---|---|
| Needle tip (g) | 24.3 (4.6) | 24.0 (3.6) |
| Needle transition (g) | 19.0 (1.0) | 19.3 (1.4) |
| Needle heel (g) | 11.3 (1.2) | 10.0 (0.5) |
| Catheter tip (g) | 19.8 (2.1) | 24.2 (2.3) |
| Catheter taper (g) | 15.5 (0.9) | 17.3 (1.8) |
| Catheter drag (g) | 4.8 (0.5) | 4.9 (0.4) |

NOTE: ( ) = standard deviation.

These results indicate that there is no adverse effect on the lubricant caused by using a quaternary ammonium salt in the lubrication system.

EXAMPLE NO. 4

Since amino-modified silicones are lubricious when applied to metal surfaces, the following lubricant solutions were prepared.

| | Lubricant I | Lubricant II |
|---|---|---|
| Silicone Surfactant | 4.50 | 4.50 |
| Amino-modified silicone polyether copolymer | 0.00 | 0.50 |
| Vitamin E (%) | 0.25 | 0.25 |
| Cosmocil (PPM) | 50 | 50 |
| Water Q.S. to | 100 | 100 |

20 gauge catheter products were assembled after dipping the catheter and the introducer needle separately into the above solutions. The tip adhesion force between the catheter and the needle was measured after aging the assemblies at 90° C. for 2½ days. The results are tabulated below:

| | Tip Adhesion (lbs) |
|---|---|
| Lubricant I | 0.348 (0.11) |
| Lubricant II | 0.188 (0.03) |

NOTE: ( ) = standard deviation.

These test results indicate that the use of an amino-modified silicone-polyether copolymer does lubricate the metal surface better than the unmodified silicone surfactant alone.

EXAMPLE NO. 5

The following statistical experiment was run to optimize the formulation of the lubrication system of this invention. The following table lists some of the composition variations used.

| | Composition A | Composition B | Composition C |
|---|---|---|---|
| Silicone Surfactant | 3.0 | 4.5 | 6.0 |
| Amino-modified silicone polyether copolymer | 0.5 | 0.25 | 0.5 |
| Vitamin E (%) | 0.125 | 0.13 | 0.125 |
| Cosmocil (PPM) | 50 | 50 | 50 |
| Water Q.S.to | 100 | 100 | 100 |

20 gauge catheter assemblies were assembled after dipping the catheters and the introducer needle separately. After aging the assemblies at 90° C. for 2½ days, these assemblies were penetration tested through thick natural latex film of 86.7 mils thickness. The thick latex was used because it is closer to the thickness of mammalian skin and because small differences in penetration forces are magnified. The results are tabulated below:

| | Composition A | Composition B | Composition C |
|---|---|---|---|
| Needle tip (g) | 156.0 (11.7) | 150.4 (13.1) | 155.9 (9.5) |
| Catheter tip (g) | 90.6 (10.3) | 87.0 (10.5) | 98.3 (7.0) |
| Catheter drag (g) | 31.6 (2.9) | 32.0 (2.3) | 27.6 (1.8) |

NOTE: ( ) = standard deviation. Sample size = 8.

The above assemblies were also aged at 90° C. for two weeks to simulate a five year shelf-life and penetration tested through fresh cow skin. The results are tabulated below:

| | Composition A | Composition B | Composition C |
|---|---|---|---|
| Needle tip (g) | 237.0 (63.7) | 226.0 (68.6) | 209.0 (46.1) |
| Catheter tip (g) | 299.0 (53.5) | 379.0 (42.7) | 378.0 (41.2) |
| Catheter taper(g) | 320.0 (37.9) | 284.0 (34.0) | 327.9 (39.4) |
| Catheter drag (g) | 51.0 (8.0) | 46.0 (9.7) | 42.0 (11.2) |

NOTE: ( ) = standard deviation. Sample size = 5.

These results on thick latex membrane show that the amount of silicone surfactant applied to the catheter and the needle has opposite effects on catheter drag and needle tip penetration. The higher the silicone surfactant concentration, the lower the drag, but at high lubricant concentrations the needle tip penetration value increases. On fresh cow skin, the needle tip penetration values decreased with increased concentration.

EXAMPLE NO. 6

The following formulations were tested.

| Catheter Lubricant | | Needle Lubricant | |
|---|---|---|---|
| Silicone Surfactant | 4.75% ± 0.25% | Silicone Surfactant | 2.38% ± 0.25% |
| Amino-modified silicone polyether copolymer | 0.525% ± 0.025% | Amino-modified silicone polyether copolymer | 0.525% ± 0.025% |
| Vitamin E | 0.263% ± 0.013% | Vitamin E | 0.263% ± 0.013% |
| Cosmocil | 50 ppm | Cosmocil | 50 ppm |
| Water Q.S. to | 100 | Water Q.S. to | 100 |

20 gauge catheters and needles were assembled as before and penetration tested through natural latex film of 13.5 mils thickness. At the same time, commercial 20 gauge Insyte® catheter products were tested under the same conditions for comparison. The results are tabulated below:

| | Experimental Sample | Commercial Sample |
|---|---|---|
| Needle tip (g) | 22.6 (8.6) | 19.5 (5.7) |
| Needle transition (g) | 17.3 (1.9) | 13.4 (1.2) |
| Needle heel (g) | 10.9 (1.1) | 7.0 (0.6) |
| Catheter tip (g) | 18.1 (3.0) | 16.3 (2.4) |
| Catheter taper (g) | 16.2 (2.1) | 10.6 (1.0) |
| Catheter drag (g) | 4.8 (1.9) | 3.0 (0.6) |

NOTE: ( ) = standard deviation. Sample size 10.

As evident, the results are comparable for the commercial product and the experimental sample. The commercial sample used polydimethylsiloxane silicone fluid as the lubricant.

EXAMPLE NO. 7

22 gauge catheters and needles were assembled as before using the formulations described in Example 6 and penetration tested through sheep skin on the hind legs just below the knee. The penetration forces were measured using sensitive force transducers. The data were collected on a computer for analysis. For comparison, commercial 22 gauge catheter and needle assemblies using polydimethylsiloxane silicone fluid as the lubricant were used. The results are summarized below:

| | Experimental Sample | Commercial Sample |
|---|---|---|
| Max. Catheter/Needle Tip (g) | 142.57 | 164.67 |
| Max. Catheter drag (g) | 70.31 | 271.68 |

As is evident, the new lubrication system is superior to the commercial product.

EXAMPLE 8

Polyurethane tubes were lubricated using the formulations of this invention described in Example 6 as well as polydimethylsiloxane silicone fluid. These tubes were implanted into the aorta of rabbits to determine the level of associated clotting and emboli formulations. After three days the animals were sacrificed and the tubes were examined while they were still in the aorta. Clotting, if present, was photographed and recorded as to size, number and location. The kidneys were also examined for renal infarcts which would indicate that emboli had formed and traveled downstream to lodge in the small arteries of the kidney. The clotting resulting from the waterbased lubricant systems of the invention was less than the clotting resulting from the commercial lubricant. The calculated risk of clotting was three times less for the waterbased lubricant versus the commercial lubricant.

Thus it is seen that a new lubrication system is provided that is inexpensive and easy to control. In addition, the lubrication system of this invention is safe, nontoxic and "environmentally friendly."

We claim:

1. A medical device having a surface with a water soluble lubricant thereon, the lubricant consisting essentially of a block copolymer polyalkylene oxide-modified polydimethylsiloxane and an amino-modified silicone-polyether copolymer.

2. A medical device having a surface with a water soluble lubricant thereon, the lubricant consisting essentially of a block copolymer polyalkylene oxide-modified polydimethylsiloxane, an amino-modified silicone-polyether copolymer and vitamin E or its derivatives.

3. A medical device having a surface with a water soluble lubricant thereon, the lubricant consisting essentially of a block copolymer polyalkylene oxide-modified polydimethylsiloxane, an amino-modified silicone polyether copolymer, vitamin E or its derivatives and polyhexamethylene biguanide hydrochloride.

* * * * *